United States Patent [19]
Momparler et al.

[11] Patent Number: 6,083,719
[45] Date of Patent: Jul. 4, 2000

[54] CYTIDINE DEAMINASE CDNA AS A POSITIVE SELECTABLE MARKER FOR GENE TRANSFER, GENE THERAPY AND PROTEIN SYNTHESIS

[75] Inventors: Richard L. Momparler, Montreal, Canada; Josée Laliberté, Chapel Hill, N.C.; Denis Cournoyer; Nicoletta Eliopoulos, both of Montreal, Canada

[73] Assignee: Hôpital Sainte-Justine, Montreal, Canada

[21] Appl. No.: 08/968,768

[22] Filed: Oct. 27, 1997

Related U.S. Application Data

[63] Continuation of application No. 08/509,138, Jul. 31, 1995, abandoned.

[51] Int. Cl.[7] .............................. C12N 5/10; C12N 15/09; C12N 15/79; C12N 15/63
[52] U.S. Cl. .................. 435/69.1; 435/320.1; 435/325; 435/375; 435/183; 435/227; 536/23.1; 536/23.5
[58] Field of Search ............................... 435/69.1, 320.1, 435/375, 7.2, 325, 354, 363, 366, 183, 227; 536/23.1, 23.5

[56] References Cited

U.S. PATENT DOCUMENTS 5,399,346  3/1995  Anderson et al. ................... 424/93.21

FOREIGN PATENT DOCUMENTS

WO 92/07943  5/1992  WIPO.

OTHER PUBLICATIONS

Laliberté et al., 1994, Cancer Res. 54: 5401–5407.
Markowitz et al., 1988, J. Virol. 62: 1120–1124.
Corey et al., 1990, Blood 75: 337–343.
Podda et al., 1992, Proc. Natl. Acad. Sci. USA 89: 9676–9680.
Ward et al., 1994, Blood 84: 1408–1414.
Chabner et al., 1990, In Cancer Chemotherapy, Principles and Practice, Lippincott Company, pp. 154–179.
Cepko 1989, In Current Protocols in Molecular Biology, pp. 9.10.1–9.11.12, Ausubel et al., Eds., Wiley & Sons.
Dwarki et al., 1995, Proc. Natl. Acad. Sci. USA 92: 1023–1027.
Chabot et al., 1983, Biochem. Pharmacol. 32: 1327–1328.
Bouffard et al., 1993, Biochem. Pharmacol. 45: 1857–1861.
Ghattas et al., 1991, Mol. Cell. Biol. 11: 5848–5859.
Boyum et al., 1994, Exp. Hematology 22: 208–214.
Kühn et al., 1993, Biochem., Biophys. Res. Com. 190: 1–7.
Sambrook et al., 1989, Molecular Cloning: A Laboratory Manual, 2nd, Cold Spring Harbor Laboratory Press, N.Y.
Steuart, et al. "Cytidine deaminase and the development of resistance to arabinosyl cytosine," Nature, vol. 233 (38): 109–110, Sep. 22, 1971.
Ohe, et al. "Combination effect of vaccination with IL–2 and IL–4 cDNA transfected cells on the induction of a therapeutic immune response against Lewis Lung carcinoma," Int. J. Cancer, vol. 53: 432–437, 1993.
Miller, A.D. "Progress toward human gene therapy," Blood, vol. 76(2): 271–278, Jul. 15, 1990.
Coghlan, A. "Gene dream fades away," New Scientist, pp. 14–15, Nov. 25, 1995.
Brown, D. "Gene Therapy 'Oversole' by Researchers, Journalists," The Washington Post, A22, Dec. 8, 1995.
Roemer, et al. "Concepts and Strategies for human gene therapy," Eur. J. Biochem., vol. 208: 211–225, 1992.

*Primary Examiner*—Karen M. Hauda
*Attorney, Agent, or Firm*—Swabey Ogilvy Renault; France Côte

[57] ABSTRACT

The present invention relates to a DNA sequence for the human cytidine deaminase that has been engineered into an eukaryotic expression vector, thereby permitting cytidine deaminase expression in mammalian cells. Cytidine deaminase expression confers resistance to cytosine nucleoside analogs, such as cytosine arabinoside, and can be used as a positive selectable marker. The expression of cytidine deaminase in cells protects them from the toxic effects of cytosine nucleoside analogs. Such a resistance provides applications for gene therapy of malignant, immune and viral diseases. A bacterial expression vector containing the gene can be used to produce cytidine deaminase in large quantities.

12 Claims, 4 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 892 base pairs
      (B) TYPE: nucleic acid
      (C) STRANDEDNESS: single
      (D) TOPOLOGY: linear    (ii) MOLECULE TYPE: cDNA    (iii) HYPOTHETICAL: NO    (iv) ANTI-SENSE: NO    (vi) ORIGINAL SOURCE:
      (A) ORGANISM: Homo sapiens
      (F) TISSUE TYPE: Myeloid
      (H) CELL LINE: HL-60

(viii) POSITION IN GENOME:
      (A) CHROMOSOME/SEGMENT: 1

(ix) FEATURE:
      (A) NAME/KEY: CDS
      (B) LOCATION: 118..558

(x) PUBLICATION INFORMATION:
      (A) AUTHORS: Laliberte, Josee
          Momparler, Richard L
      (B) TITLE: Human Cytidine Deaminase: Purification of
          Enzyme, Cloning, and Expression of its
          complementary DNA
      (C) JOURNAL: Cancer Research
      (D) VOLUME: 54
      (F) PAGES: 5401-5407
      (G) DATE: October 15-1994
      (K) RELEVANT RESIDUES IN SEQ ID NO:1: FROM 1 TO 922

(xi) SEQUENCE DESCRIPTION: SEQ ID NO:1:

```
GCGCGCCAGT TTCAGGATGC AGGGTCTAGG AGAGGAGCCG CAATCGTGTC TGGGGCCCCA      60

GCCAGGCTGG CCGGAGCTCC TGTTTCCGCT GCTCTGCTGC CTGCCCGGGG TACCAAC        117

ATG GCC CAG AAG CGT CCT GCC TGC ACC CTG AAG CCT GAG TGT GTC CAG      165
Met Ala Gln Lys Arg Pro Ala Cys Thr Leu Lys Pro Glu Cys Val Gln
  1               5                  10                  15

CAG CTG CTG GTT TGC TCC CAG GAG GCC AAG AAG TCA GCC TAC TGC CCC      213
Gln Leu Leu Val Cys Ser Gln Glu Ala Lys Lys Ser Ala Tyr Cys Pro
             20                  25                  30

TAC AGT CAC TTT CCT GTG GGG GCT GCC CTG CTC ACC CAG GAG GGG AGA      261
Tyr Ser His Phe Pro Val Gly Ala Ala Leu Leu Thr Gln Glu Gly Arg
         35                  40                  45

ATC TTC AAA GGG TGC AAC ATA GAA AAT GCC TGC TAC CCG CTG GGC ATC      309
Ile Phe Lys Gly Cys Asn Ile Glu Asn Ala Cys Tyr Pro Leu Gly Ile
     50                  55                  60

TGT GCT GAA CGG ACC GCT ATC CAG AAG GCC GTC TCA GAA GGG TAC AAG      357
Cys Ala Glu Arg Thr Ala Ile Gln Lys Ala Val Ser Glu Gly Tyr Lys
 65                  70                  75                  80

GAT TTC AGG GCA ATT GCT ATC GCC AGT GAC ATG CAA GAT GAT TTT ATC      405
Asp Phe Arg Ala Ile Ala Ile Ala Ser Asp Met Gln Asp Asp Phe Ile
                 85                  90                  95

TCT CCA TGT GGG GCC TGC AGG CAA GTC ATG AGA GAG TTT GGC ACC AAC      453
Ser Pro Cys Gly Ala Cys Arg Gln Val Met Arg Glu Phe Gly Thr Asn
                100                 105                 110
```

```
TGG CCC GTG TAC ATG ACC AAG CCG GAT GGT ACG TAT ATT GTC ATG ACG        501
Trp Pro Val Tyr Met Thr Lys Pro Asp Gly Thr Tyr Ile Val Met Thr
        115                 120                 125

GTC CAG GAG CTG CTG CCC TCC TCC TTT GGG CCT GAG GAC CTG CAG AAG        549
Val Gln Glu Leu Leu Pro Ser Ser Phe Gly Pro Glu Asp Leu Gln Lys
        130                 135                 140

ACT CAG TGA CAGCCAGAGA ATGCCCACTG CCTGTAACAG CCACCTGGAG                598
Thr Gln *
145

AACTTCATAA AGATGTCTCA CAGCCCTGGG GACACCTGCC CAGTGGCCCC AGCCTACAGG      658

GACTGGGCAA AGATGATGTT TCCAGATTAC ACTCCAGCCT GAGTCAGCAC CCCTCCTAGC      718

AACCTGCCTT GGGACTTAGA ACACCGCCGC CCCCCTGCCC CACCTTTCCT TTCCTTCCTG      778

TGGGCCCTCT TTCAAAGTCC AGCCTAGTCT GGACTGCTTC CCCATCAGCC TTCCCAAGGT      838

TCTATCCTGT TCCGAGCAAC TTTTCTAATT ATAAACATCA CAGAACATCC TGGA            892
```

(2) INFORMATION FOR SEQ ID NO:2:

(i) SEQUENCE CHARACTERISTICS:
        (A) LENGTH: 146 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Ala Gln Lys Arg Pro Ala Cys Thr Leu Lys Pro Glu Cys Val Gln
 1               5                  10                  15

Gln Leu Leu Val Cys Ser Gln Glu Ala Lys Lys Ser Ala Tyr Cys Pro
            20                  25                  30

Tyr Ser His Phe Pro Val Gly Ala Ala Leu Leu Thr Gln Glu Gly Arg
        35                  40                  45

Ile Phe Lys Gly Cys Asn Ile Glu Asn Ala Cys Tyr Pro Leu Gly Ile
    50                  55                  60

Cys Ala Glu Arg Thr Ala Ile Gln Lys Ala Val Ser Glu Gly Tyr Lys
65                  70                  75                  80

Asp Phe Arg Ala Ile Ala Ile Ala Ser Asp Met Gln Asp Asp Phe Ile
                85                  90                  95

Ser Pro Cys Gly Ala Cys Arg Gln Val Met Arg Glu Phe Gly Thr Asn
            100                 105                 110

Trp Pro Val Tyr Met Thr Lys Pro Asp Gly Thr Tyr Ile Val Met Thr
        115                 120                 125

Val Gln Glu Leu Leu Pro Ser Ser Phe Gly Pro Glu Asp Leu Gln Lys
    130                 135                 140

Thr Gln
145
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "dna"

(iii) HYPOTHETICAL: NO (xi) SEQUENCE DESCRIPTION: SEQ ID NO:3:

TACCACCATG GCCCAGAAGC GT                                           22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "dna"

(iii) HYPOTHETICAL: NO

(xi) SEQUENCE DESCRIPTION: SEQ ID NO:4:

TGGGCAGGAT CCGGCTGTCA CT                                           22

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "dna"

(iii) HYPOTHETICAL: NO

(xi) SEQUENCE DESCRIPTION: SEQ ID NO:5:

GGTGGACCAT CCTCTAGACT G                                            21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "dna"

(iii) HYPOTHETICAL: NO

(xi) SEQUENCE DESCRIPTION: SEQ ID NO:6:

AGCAGCTCCT GGACCGTCAT G                                            21

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "dna"

(iii) HYPOTHETICAL: NO

(xi) SEQUENCE DESCRIPTION: SEQ ID NO:7:

ACGGGATCCA TGGCCCAGAA GCGTCCTG                                     28

(2) INFORMATION FOR SEQ ID NO:8:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "dna"

(iii) HYPOTHETICAL: NO (xi) SEQUENCE DESCRIPTION: SEQ ID NO:8:

CCGCTCGAGT CACTGAGTCT TCTGCAG                                          27
```

CYTIDINE DEAMINASE CDNA AS A POSITIVE SELECTABLE MARKER FOR GENE TRANSFER, GENE THERAPY AND PROTEIN SYNTHESIS

This application is a continuation of application Ser. No. 08/509,138 filed on Jul. 31, 1995 now abandoned.

BACKGROUND OF THE INVENTION i) Field of the Invention

This invention relates to a human nucleic acid for cytidine deaminase that has been engineered into eukaryotic and bacterial expression vectors, to the expression of human cytidine deaminase by mammalian cells and bacterial cells, and to cells expressing human cytidine deaminase. The invention further relates to methods and gene therapies that employ the dominant selectable marker, cytidine deaminase, which has the ability to inactivate a toxic antimetabolite such as cytosine arabinoside by deamination to uracil arabinoside.

ii) Description of the Prior Art

Selectable markers are important tools in the study, regulation and function of genes and are potentially important in gene transfer therapies. Conferring a unique resistance to a cytotoxic agent enables the skilled artisan the ability to select genetically altered cells from a mixed population.

The enzyme cytidine deaminase (CD) has the ability to catalyze the deamination of cytosine arabinoside, an antimetabolite that is toxic to mammalian cells, to uracil arabinoside which is non-toxic at pharmacological concentrations (Chabner, et al., 1990, In Cancer Chemotherapy: Principles and Practice pp. 154–179, Lippincott Company). CD can also inactivate, by deamination, other cytosine nucleoside analogs that are currently used as anticancer agents (Chabot et al., 1983, Biochem. Pharmacol. 32: 1327–1328; Bouffard et al., 1993, Biochem. Pharmacol., 45: 1857–1861). In mammalian cells cytosine arabinoside (ARA-C), is metabolized to ARA-CMP, ARA-CDP and ARA-CTP, the latter nucleotide analog is incorporated into DNA, producing a potent inhibition of DNA synthesis and resulting in growth inhibition and cell death (Chabner, et al., 1990, In Cancer Chemotherapy: Principles and Practice pp 154–179, Lippincott Company).

The availability of a dominant selectable marker to cytosine analogs, would be a significant advantage for the skilled artisan in the field of molecular biology, cell biology and gene transfer technology in eukaryotes.

The efficacy of treatments of patients with cytosine nucleoside analogs, suffers from the relatively high doses of cytosine analogs required and the accompanying side effects resulting from normal cell cytotoxicity. Indeed, bone marrow suppression is the major dose-limiting toxicity produced by intensive chemotherapy with ARA-C and related cytosine nucleoside analogs.

It would thus be advantageous for the patient and clinician if susceptible cells, such as bone marrow cells could be protected from the toxic effects of the cytosine analog. This protection could permit an increase in the therapeutic index of the drug. In addition, it could permit an increase in the dose administered without substantially increasing the side effects of the drug. A similar approach has been reported for the establishment of methotrexate-resistant bone marrow cells (Corey, et al., 1990, Blood 75: 337–343).

A partial cDNA for human CD has been isolated and the expression of cytidine deaminase demonstrated in bacteria but not in eukaryotic cells (Kühn, et al., 1993, Biochem. Biophys. Res. Com. 190: 1–7). Recently, the full-length human cDNA has been isolated and its DNA and amino acid sequence determined (Laliberté et al., 1994, Cancer Res. 54: 5401–5407). Having the full-length human cDNA for CD, it would be advantageous to engineer vectors permitting expression of cytidine deaminase in cells. It would also be beneficial to obtain bone marrow cells expressing human CD and implant them in a patient suffering form an immune disease, prior to the treatment of this patient with cytosine analogs. This kind of gene therapy and others, could be beneficial for the treatment of diseases including but not limited to acute T-cell disorders, rheumatoid arthritis, and autoimmune diseases. Gene therapy using CD could also be beneficial for preventing graft rejection.

Cytidine deaminase has been reported to inhibit the proliferation of myeloid hematopoietic cells (Boyum et al., 1994, Exp. Hematology, 22: 208–214). This enzyme could thus have therapeutic use in the treatment of certain types of leukemia.

It would be advantageous to obtain large amounts of human cytidine deaminase to test the therapeutic potential of the enzyme. In addition, it would be beneficial to obtain cells expressing CD, as they could be used to test for inhibitors or up-regulators of cytidine deaminase activity.

SUMMARY OF THE INVENTION

It is an object of this invention to provide a new positive selectable marker, resistance to cytosine analogs, through the expression of a nucleic acid for human CD. When integrated into a eukaryotic expression vector and expressed in mammalian cells, cytidine deaminase confers to the transfected cell a unique resistance to the cytotoxic effects of ARA-C and related cytosine nucleoside analogs.

It is a further object of the present invention to provide a host cell comprising a nucleic acid construct which permits expression of human cytidine deaminase. The invention also seeks to provide expression vectors harboring the cytidine deaminase nucleic acid segment of the invention in an expressible from, and cells transformed with same. Such cells can serve a variety of purposes such as in vitro models for the function of CD as well as for screening pharmaceutical compounds that could regulate the expression of the CD gene or the activity of the protein encoded therefrom. An expression vector harboring the CD nucleic acid segment or part thereof, can be used to obtain substantially pure protein or a peptide fragment therefrom. The purified enzyme or peptide fragment may be used as a therapeutic agent to inhibit proliferation of certain types of leukemia. An example of a construct expressing CD is the DNA plasmid construct designated pMFG-CD.

Well-known vectors can be used to obtain large amounts of the protein which can then be purified by standard biochemical methods based on charge, molecular weight, solubility or affinity of the protein or alternatively, the protein can be purified by using gene fusion techniques such as GST fusion, which permits the purification of the protein of interest on a gluthathion column. Other types of purification methods or fusion proteins could also be used.

It is also contemplated to provide shuttle vectors, comprising a nucleic acid sequence encoding human cytidine deaminase capable of expression in eukaryotic cells as well as sequences expressible in microorganisms. Such vectors are designed to confer a selective advantage in both the eukaryotic and prokaryotic cells harboring them.

Antibodies both polyclonal and monoclonal can be prepared from the protein encoded by the CD nucleic acid segment of the invention. Such antibodies can be used for a variety of purposes including affinity purification of the CD protein and to determine the level of expression of the cytidine deaminase protein in cells. The latter could be of use for the indirect determination of the resistance of cancer cells to ARA-C and related cytosine analogs for example. It is also contemplated that sequences from the human CD nucleic acid sequence, variants or homologs thereof, or oligonucleotides derived from these nucleic acid sequences, could also be used to determine the level of expression of cytidine deaminase in cells. Such an information could, for example, be used to orient the chemotherapeutic treatment profile of a patient.

It is yet a further object of this invention to provide in vitro methods for the selection of clones in a mixed population of cells. These methods can be used for gene transfer. In addition, selected cell clones can be used in vivo for gene transfer therapies.

It is still a further object of this invention to provide therapeutic methods for malignant, immune and viral diseases, based on an expression of a human nucleic acid encoding CD or a variant thereof retaining cytidine deaminase activity, and a chemotherapeutic treatment with cytosine nucleoside analogs.

More specifically, it is another object of the present invention to provide a cytidine deaminase positive selection system for gene transfer therapies comprising the steps of inserting the nucleic acid sequence comprising the human cytidine deaminase gene or variant thereof in a eukaryotic expression vector, along with an exogenous nucleic acid sequence to be expressed, transfecting this construct into a host genome and treating the host or parts thereof with ARA-C or related cytosine nucleoside analogs in pharmacologically acceptable doses, so as to select cells that have integrated the construct into their genome. Examples of products encoded by exogenous nucleic acid sequences include but are not limited to tumour suppressor genes, growth factors and single chain antibodies to specific proteins.

In a further embodiment, it is an object of the invention to provide a method of administering allogenic or autologous bone marrow cells into a patient comprising the steps of treating the bone marrow cells with a cytidine deaminase construct packaged into a vector in such a manner that the construct will preferentially confer resistance to ARA-C and related cytosine nucleoside analogs to the bone marrow cells. Administering the treated bone marrow cells to a patient and subsequently administering toxic doses of ARA-C or related cytosine nucleoside analogs such that tumor cells or abnormal lymphocytes are destroyed, whereas the transplanted bone marrow cells survive, thereby reducing the bone marrow toxicity produced by these analogs.

In addition, it is an object of the present invention to provide the human cytidine deaminase nucleic acid, sequences hybridizing thereto under high stringency conditions, a corresponding sequence within the scope of the degeneracy of the genetic code or a functional variant of such a nucleic acid sequence.

In addition, it is an object of this invention to provide retroviral particles, containing the human cytidine deaminase nucleic acid. These retroviral particles can be used to infect cells, such as normal hematopoietic stem cells in vitro, to confer resistance to ARA-C and related cytosine nucleoside analogs. Through infusion of these cells into a patient, the patient now possesses cells that are protected from the cytotoxic effects of a chemotherapeutic treatment with cytosine analogs such as ARA-C.

The designation functional variant is to be interpreted as meaning that the variant retains the biological activity of the protein from which it might originate. As used herein, the term "oligonucleotide" includes both oligomers of ribonucleotides and oligomers of deoxyribonucleotides.

The designation related cytosine analogues as used herein is meant to include without being limited thereto: 2,2'-difluorodeoxycytidine and 5-aza-2'-deoxycytidine.

The term high stringency hybridization conditions, as used herein and well known in the art, includes, for example: 5×SSPE (1×SSPE is 10 mM Na-phosphate, pH 7.0; 0.18 M NaCl; 1 mM $Na_2$ EDTA), 5×Denhardt's solution (from a 100×solution containing 2% BSA, 2% Ficoll, 2% polyvinyl pyrollidone), 0.1% SDS, and 0,5 mg/ml denatured salmon sperm DNA, at 65° C. Other conditions considered stringent include the use of formamide. An example of washing conditions for the blot includes, as a final stringency wash, an incubation of the blot at 65° C. in 0.1×SSPE, 0.1% SDS for 1 hour.

From the specification and appended claims, it should be understood that the term nucleic acid should be taken in a broad sense so as to include, while not being limited thereto, the cDNA and the gene encoding CD. In addition, the term gene as used herein should be interpreted so as to include the cDNA thereof. The term pharmaceutical composition should be interpreted as including veterinary compositions.

In accordance with one aspect of the invention there is provided a eukaryotic expression vector comprising the human cytidine deaminase nucleic acid sequence as set forth in SEQ. ID NO: 1, a complement thereof, a functional variant thereof due to the degeneracy of the genetic code or a nucleotide sequence which hybridizes to SEQ. ID NO: 1, complement thereof, or variant thereof under stringent conditions, wherein the cytidine deaminase nucleic acid sequence is functionally positioned in the eukaryotic expression vector so as to be expressed in a eukaryotic host cell.

In accordance with another aspect of the invention there is provided a method of conferring resistance to cytosine arabinoside or related cytosine analogs to a eukaryotic cell, the method comprising the steps of: a) introducing into the eukaryotic cell, a DNA construct comprising the human cytidine deaminase nucleic acid sequence as set forth in SEQ. ID NO: 1, a complement thereof, a functional variant thereof due to the degeneracy of the genetic code or a nucleotide sequence which hybridizes to SEQ. ID NO: 1, complement thereof, or variant thereof under stringent conditions, wherein the cytidine deaminase nucleic acid sequence confers resistance to cytosine arabinoside or related cytosine analogs when expressed in the eukaryotic cell; b) growing the eukaryotic cell of a) under conditions conducive to expression of said human cytidine deaminase nucleic sequence in the presence of cytosine arabinoside or related cytosine analogs at a concentration which is toxic to the eukaryotic cell not expressing the nucleic acid sequence; and c) selecting cytidine deaminase-expressing cells which are resistant to cytosine arabinoside or related cytosine analogs.

In accordance with still another aspect of the invention there is provided a eukaryotic cell harboring the eukaryotic expression vector comprising the human cytidine deaminase nucleic acid sequence as set forth in SEQ. ID NO: 1, a complement thereof, a functional variant thereof due to the degeneracy of the genetic code or a nucleotide sequence which hybridizes to SEQ. ID NO: 1, complement thereof, or variant thereof under stringent conditions, wherein the cytidine deaminase nucleic acid sequence is functionally positioned in the eukaryotic expression vector so as to be expressed in a eukaryotic host cell.

In accordance with yet another aspect of the invention there is provided a DNA construct comprising the human cytidine deaminase nucleic acid sequence as set forth in SEQ. ID NO: 1, a complement thereof, or a functional variant thereof due to the degeneracy of the genetic code, as well, there is provided a bacterial cell harboring such a DNA construct.

In accordance with a still further aspect of the invention there is provided a method of animal gene therapy which comprises: a) introducing into a eukaryotic cell sensitive to cytosine arabinoside or related cytosine analogs, a DNA construct comprising the human cytidine deaminase nucleic acid sequence as set forth in SEQ. ID NO: 1, a complement thereof, a functional variant thereof due to the degeneracy of the genetic code or a nucleotide sequence which hybridizes to SEQ. ID NO: 1, complement thereof, or variant thereof under stringent conditions, wherein the cytidine deaminase nucleic acid sequence confers resistance to cytosine arabinoside or related cytosine analogs when expressed in the eukaryotic cell; b) introducing the cells of a) into the animal; and c) treating the animal locally or systematically with a pharmacologically acceptable dose of cytosine arabinoside or related cytosine analogs; such that the eukaryotic cells having been rendered resistant to a treatment with cytosine arabinosides or related cytosine analogs are substantially protected from the cytotoxic effects thereof, and thereby reduce undesired side effects associated with said treatment.

In accordance with yet another aspect of the invention, there is provided a eukaryotic expression vector containing a dominant selectable marker capable of expression in a eukaryotic cell comprising: a) the nucleic acid sequence as set forth in SEQ. ID NO: 1, a complement thereof, a functional variant thereof due to the degeneracy of the genetic code or a nucleotide sequence which hybridizes to SEQ. ID NO: 1, complement thereof, or variant thereof under stringent conditions, wherein the cytidine deaminase nucleic acid sequence confers resistance to cytosine arabinoside or related cytosine analogs when expressed in the eukaryotic cell; b) a pBR322 origin of replication; and c) a promoter sequence.

In accordance with an additional aspect of the invention there is provided a dominant selectable marker for eukaryotic cells comprising the human cytidine deaminase amino acid sequence as set forth in SEQ. ID NO: 2 or a functional variant thereof, wherein said sequence confers resistance to cytosine arabinoside or related cytosine analogues when expressed in said eukaryotic cell.

Other features and advantages of the invention will be apparent from the description of the preferred embodiments given hereinafter and from the claims.

DETAILED DESCRIPTION OF THE INVENTION

The present invention relates, in part, to the insertion of the human cytidine deaminase cDNA into a eukaryotic expression vector. A principle embodiment of this aspect of the present invention relates to the successful expression of the CD cDNA in mammalian cells and the subsequent resistance to the toxic effects of ARA-C and related cytosine nucleoside analogs provided by the cDNA. The present invention also relates to methods that apply to the above CD gene as a selectable marker in gene transfer studies and therapies. In particular, the present invention relates to the human cDNA for CD in an eukaryotic expression vector, for example, pMFG and the expression of the cDNA in mammalian cells, for example, murine fibroblasts.

In mammalian cells cytidine deaminase converts cytidine to uridine and probably serves the purpose to maintain a balance of pyrimidine nucleotides in the ribonucleotide and deoxyribonucleotide pools.

The distinguishing feature of the present invention is the expression of the CD cDNA in eukaryotic cells for the purpose of creating a positive selection system. One skilled in the art of molecular biology may express the CD cDNA in a variety of eukaryotic expression vectors to achieve the same purposes as those disclosed herein.

Introduction of the CD cDNA into mammalian cells results in the ability of the mammalian transfected cells to convert cytidine to uridine; normally most mammalian cells contain only low levels of the enzyme cytidine deaminase. An increased in vitro conversion of radiolabelled cytidine to uridine is consistently seen in transfected cells. The presence and expression of the CD cDNA has no apparent deleterious effects upon the cells. However, when such cells are exposed to ARA-C they show resistance to inhibition of colony formation and to inhibition of DNA synthesis produced by this cytosine nucleoside analog. Normal cells that do not express or express low level of cytidine deaminase are sensitive to all these inhibitory effects produced by ARA-C.

The present invention is the first to demonstrate that a eukaryotic enzyme for cytidine deaminase (i.e.: the human enzyme) can, upon transfection into cells, render them resistant to ARA-C. The transfection can be performed by a great variety of methods including but not limited thereto to calcium phosphate transfection, electroporation and retroviral transfection. The nucleic acid sequences encoding CD can remain unintegrated as part of an episome or can be inserted into the genome. By providing a method of rendering eukaryotic cells, and more preferably mammalian cells, resistant to ARA-C by virtue of the expression of the cytidine deaminase cDNA, one skilled in the art will be enabled to apply the cytidine deaminase positive selection system (CDPSS) to a variety of tissues by simply applying known techniques in molecular biology and retrovirology.

Another way to confer tissue specificity may be to deliver the CDPSS using the pMFG-CD plasmid in different packaging cell lines, an example of such a cell line is GP+E86. A variety of retrovirus packaging lines which have different cell-type and species tropisms have been described (Cepko, 1989, In Current Protocols in Molecular Biology, pp 9.10.1–9.11.12, Ausubel et al., Eds., Wiley & Sons).

One skilled in the art of molecular biology will have no difficulty adapting the teachings of this invention in order to transfect a different packaging cell line, thereby potentially changing the target cell specificity of the CDPSS.

The CDPSS system can be modified by someone skilled in the art to incorporate the CDPSS and the therapeutic gene in the same vector. There are several ways of accomplishing this modification. One example would be to clone a therapeutic gene next to the CD cDNA in pMFG-CD. The expression of both genes could be accomplished by the insertion of the internal ribosomal entry site between the two genes (Ghattas et al., 1991, Mol. Cell. Biol. 11: 5848–5859). Any cell altered by the vector would then contain the CD cDNA and the therapeutic gene. Alternatively, the nucleic acid sequence to be expressed can be harbored by a different vector than that harboring the CD nucleic acid sequence, the two vectors can be co-transfected using a variety of well known methods (In Current Protocols in Molecular Biology, 1989, Ausubel et al., Eds., Wiley & Sons) The co-transfected vector can be a viral or non-viral plasmid.

The present invention further relates to the creation of novel double positive selection vectors. The CD nucleic acid sequence of the present invention can be inserted along with the mutated human dihydrofolate reductase gene (Corey et al., 1990, Blood 75: 337–343) into a gene transfer vector. The cells receiving the vector are rendered resistant to ARA-C or analogs thereof and methotrexate, thereby providing a double positive selection system for protecting cells from the toxic effects of two different antimetabolites. It is also contemplated herein, that a double selection system can be dependent on the presence of the CD nucleic acid sequence of the present invention and that of the mutated human dihydrofolate reductase gene (DHFR), on different vectors. Similarly, analogs of DHFR, or other dominant selectable markers can be used in a double (or more) selection system. Other examples of dominant selectable markers include but are not limited to a neomycin gene conferring resistance to G418, the gpt gene, conferring resistance to mycophenolic acid and a multidrug resistance gene, conferring resistance to a variety of drugs such as adriamycin, colchicine and vincristine.

In another embodiment, the present invention relates to a therapeutic method for the treatment of cancer, viral and immune diseases. This invention relates to making normal bone marrow cells resistant to the toxic effects of chemotherapy, for example ARA-C. This can be accomplished by gene transfer of CD into normal bone marrow cells and transplantation of these cells into the animal to be treated. It will then be possible to administer higher doses of ARA-C to this animal to obtain a superior therapeutic effect without encountering unacceptable bone marrow toxicity (Corey et al., 1990 Blood, 75: 337–343; Podda et al., 1992, Proc. Natl. Acad. Sci. USA 89: 9676–9680; and Ward et al., 1994, Blood. 84: 1408–1414). In a preferred embodiment, the animal is a human patient. In another preferred embodiment, the human patient undergoes cancer therapy with ARA-C or related cytosine analogs.

Thus, it is possible to make use of the discovery that expression of the human cytidine deaminase cDNA is mammalian cells confers thereupon resistance to a cytosine arabinoside or selected cytosine analogs in the following four main contexts:

A. as a dominant selectable marker;
B. as a diagnostic tool;
C. in the design of new drugs; and
D. in gene therapy.

A. Dominant Selectable Marker

When properly expressed, the cDNA clone described allows the production of a dominant selectable trait. Indeed, when the nucleic acid sequence as set forth in SEQ. ID NO: 1, or a functional variant or homologue thereof, is introduced into a drug-sensitive cell under conditions appropriate for its expression, the drug-sensitive cell becomes drug resistant and is able to survive and form colonies even in media containing drug levels which normally cause death of drug-sensitive cells.

The cytidine deaminase nucleic acid sequence of the present invention can also be used as a vehicle for moving hybrid genes into new host cells and monitoring their presence. It is thus possible to engineer a DNA sequence which includes the cytidine deaminase gene and at least one gene of interest into a plasmid, and introduce this plasmid into a host cell, monitoring the presence of the plasmid in these cells by culturing in media containing cytosine arabinoside or related cytosine analogs. Cells which contain the cytidine deaminase gene and the gene(s) of interest will survive and those which do not will die.

B. Diagnostic Tool

The nucleic acid sequence of the cytidine deaminase or parts thereof can be used to assess the level of expression of this gene in tissues or cells. For example, the RNA can be isolated from tumour cells and through Northern blot analysis (Sambrook et al., 1989) the level of expression of the cytidine deaminase gene can be measured to assess the level of expression thereof. Such an information can be advantageous for monitoring the resistance of the tumour to the chemotherapeutic regimen. Another method for measuring the level of expression includes in situ hybridization.

Antibodies raised against cytidine deaminase protein can also be used in a diagnostic context. Such antibodies, whether polyclonal or monoclonal can be used in different types of immuno-assays to measure the level of expression of cytidine deaminase protein.

Using large amounts of cytidine deaminase, obtained for example through the expression of the pGEX-4T-1 vector, the protein or segment thereof can be used in standard antibody production techniques using for example, a rabbit or a rat as a host. If monoclonal antibodies are produced, the well-known techniques involving fusion to form hybridomas would be used.

C. Design of New Drugs

The above information makes it possible to design new drugs or modify presently available drugs to increase their activity toward drug-resistant cells, or to design a cytidine deaminase which is more efficient at detoxifying cytosine arabinoside or related cytosine analogs. In addition, the present information makes it also possible to screen for inhibitors of cytidine deaminase. For example, purification of large quantities of mature cytidine deaminase will allow study of the three dimensional structure thereof. Combined with the availability of multiple antibodies directed towards segments of this protein, it will be possible to define the specific mechanism imparting drug resistance and permit the design of new drugs, or modification of old ones affecting the action of the protein, or alternatively design modified protein interacting differently with these drugs.

D. Gene Therapy

Because of the extensive depletion of bone marrow which occurs when a patient is treated with chemotherapeutic drugs, the patient is unable to fight-off a variety of bacterial, fungal and viral pathogens. The cDNA of the present invention or variants thereof can be used to alleviate this problem. This can be accomplished by inserting the cDNA described or variants thereof into appropriate amphotropic or ecotropic retroviral constructs which can then be used to infect normal bone marrow cells. This approach can be valuable in a situation in which bone marrow is removed from a patient, the gene inserted in vitro and the resulting engineered marrow reintroduced into the patient (autologous treatment). Insertion of heterologous marrow is also contemplated.

The treatment of the marrow can also be valuable in bone marrow transplants, in which the patient's initial bone marrow is replaced by marrow into which the cytidine deaminase cDNA or functional variant thereof has been incorporated.

Thus, in these examples, the engineered bone marrow cells are resistant to the effects of a chemotherapeutic regimen with cytosine arabinoside or related cytosine analogs and are thus able to repopulate the depleted marrow. The addition of further dominant selectable markers, adapted to a particular chemotherapeutic regimen would also be beneficial. Thus, it will be possible to administer higher concentrations of the chemotherapeutic drug(s) to the individual without destroying the transplanted bone marrow. This would contribute to the ability of the patient to survive.

Molecular Biology Techniques

Plasmid pDR2 contains the complete cDNA sequence for human cytidine deaminase (Laliberté et al., 1994, Cancer Res. 54: 5401–5407, the context of which is incorporated by reference; Gene Bank accession number L27943). Briefly, pDR2 was obtained by screening a human liver cDNA library in lambdaDR2 phage (Clontech) with radiolabelled probes. The probes were obtained by peptide sequencing from purified CD protein. Briefly, a cytidine deaminase precipitate was obtained from homogenized human placenta (fraction I). The precipitate was resuspended (fraction II), incubated in a 75° C. water bath and rapidly cooled. After centrifugation, the supernatant was recovered and concentrated (Amicon Centriprep-30™) to give fraction III. Fractions III to VI were purified by coloumn chromatography (Sephacryl S-200™ gel filtration, PAER-1000™ ion exchange, and Mono-Q™ ion exchange chromatography at pH 6.2 and 7.5). The final step used in the chromatography yielded a single peak of CD activity to give fraction VII (Laliberté et al., 1994, Cancer Res. 54: 5401–5407). Clostripain digestion or mild acid cleavage permitted the generation of peptides, which were purified and submitted to automated Edman degradation in a Porton Protein/Peptide MicroSequencer™. Some peptides were cleaved with cyanogen bromide prior to sequencing. The amino acid sequences of one such peptide (E) permitted the design of oligonucleotides.

PCR reaction using these different oligonucleotides were performed in the presence of cDNA from the HL-60 human cDNA library. The PCR products were purified using the Magic PCR Preps DNA Purification System™ (Promega) and cloned in pCRII plasmid using the TA Cloning kit™ (Invitrogen). Sequencing of a 470 bp PCR product harbored in pCRII permitted the identification of a DNA sequence encoding the codons for peptide E (Laliberté et al., 1994, Cancer Res. 54: 5401–5407). Sequencing was carried out using the Sequenase™ 2.0 kit from USB. The sequencing data obtained with this PCR product, permitted the design of 5' and 3' oligonucleotide primers which were used to amplify by PCR a specific DNA probe from liver cDNA (364 bp). This 364 bp probe was radiolabelled and used to screen the HL-60 cDNA phage library mentioned above. One positive clone was detected and converted to a plasmid (pDR2) using the method of Clontech.

Figure 1:
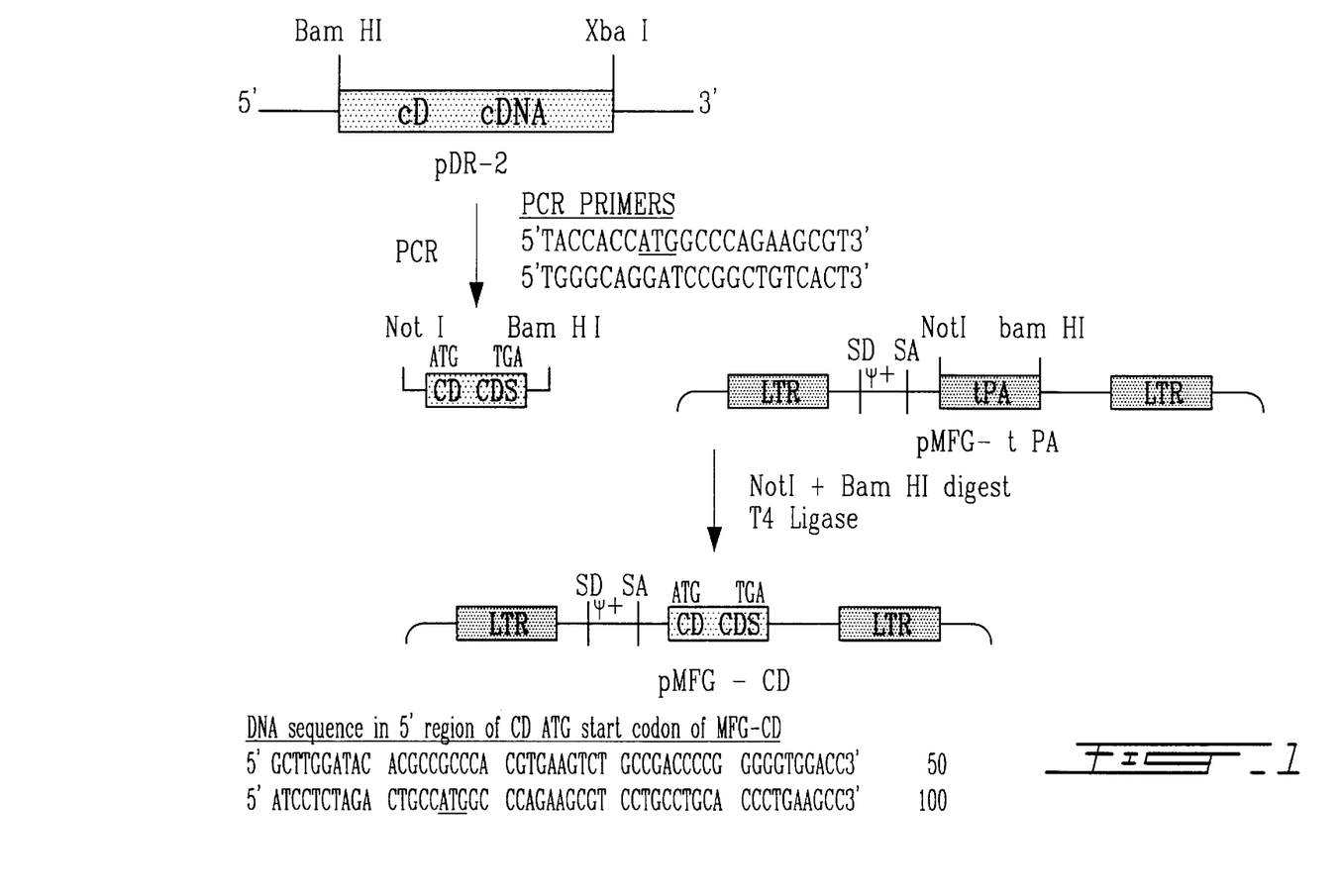
FIG. 1 shows the construction of pMFG-CD.

The insert size of this plasmid was estimated at approximately 950bp and was sequenced in both orientation by the chain termination method using fluoro-dATP and a Pharmacia A.L.F. automatic sequencer™. The 910-bp clone contained 117-bp 5'-nontranslated sequence, an open reading frame of 438-bp, and a 336-bp 3'-nontranslated region ending with a poly(A)+ tail (SEQ. ID NO: 1). The translated region predicts an open reading frame of 146 codons (SEQ. ID NO: 2) having a [predicted molecular mass of 16.2 kDa. For the plasmid pMFG-tPA the Moloney murine leukemia virus long terminal repeat (LTR) sequences are used to generate both a full length viral RNA (for encapsidation into virus particles) and a subgenomic mRNA which is responsible for the expression of inserted sequences (Dwarki et al., 1995, Proc. Natl. Acad. Sci. USA, 92: 1023–1027; and Guild et al., WO92/07943, published May 14, 1992). Protein coding sequences are inserted between the NcoI and BamHI sites. No selectable marker exists in the vector. The pSV-neo vector contains the SV40 early promoter and the neomycin phosphotransferase (neo) gene. The neo gene allows cells to survive in the presence of the protein synthesis inhibitor, neo or its analog G418 (In Current Protocols in Molecular Biology, 1989, Ausubel et al. Eds., John Wiley & Sons). These vectors and the subsequent constructs are depicted in FIG. 1.

Oligonucleotides were synthesized on a Pharmacia Gene Assembler Plus™ Instrument (Sambrook et al., 1989, Molecular Cloning: A Laboratory Manual, 2nd, Cold Spring Harbor Laboratory Press, Cold Spring Harbor, N.Y). Oligonucleotides 5'-TAC CAC CAT GGC CCA GAA GCG T-3' (SEQ. ID NO: 3) and 5'-TGG GCA GGA TCC GGC TGT CAC T-3' (SEQ. ID NO: 4) were used as primers and pDR-2 as the DNA template in a polymerase chain reaction (PCR) using the MJ Research thermocycler. SEQ. ID NO: 3 contains a NcoI recognition site at its 5' end as well as the first 5 codons of the human CD cDNA in the sense orientation. SEQ. ID NO: 4 contains a BamHI recognition site at its 5' end and the last 2 codons of the human CD cDNA in the antisense orientation. The 465 bp amplified DNA and pMFG-tPA were digested with NcoI and BamHI, purified by agarose gel electrophoresis and ligated with T4 DNA ligase according to known methods (Sambrook et al., 1989). Competent *E. coli* were transformed with the construct and individual colonies of transformants were screened for insertion by PCR and restriction enzyme digests, following standard procedures. Large scale preparation of plasmids were produced by standard methods and the plasmids purified by Quiagen™ columns (J. Sambrook et al., 1989). The resulting plasmid with the CD cDNA is called pMFG-CD. The 5' region of the cDNA was sequenced by the dideoxynucleotide chain termination method using a Pharmacia Automatic DNA Sequencer™ with fluoro-dATP to verify the sequence (In Current Protocols in Molecular Biology, 1989, Ausubel et al., Eds. Wiley & Sons).

In order to verify the integration of the CD cDNA into the genomic DNA of the transfected cells the oligonucleotide 5'-GGT GGA CCA TCC TCT AGA CTG-3' (SEQ. ID NO: 5) and 5'-AGC AGC TCC TGG ACC GTC ATG-3' (SEQ. ID NO: 6) were used as primers with ~1 ng of genomic DNA in the PCR to amplify a specific 421 bp fragment, as predicted by the DNA sequence of the pMFG-CD construct. The sense oligonucleotide SEQ. ID NO: 5 was ~70 bp downstream from the splice acceptor (SA) region of MFG. The antisense oligonucleotide SEQ. ID NO: 6 was from positions 377–397 of the CD coding region. Genomic DNA was isolated from the GP+E86 cells with In ViSorb DNA Kit™ (ID Laboratory) by cell lysis with guanidine thiocyanate and DNA adsorption on silica gel (In Current Protocols in Molecular Biology, 1989).

In order to clone the CD cDNA in a bacterial expression vector the coding region from pDR-2 was amplified by PCR using oligonucleotides 5'-ACG GGA TCC ATG GCC CAG AAG CGT CCT G-3' (SEQ. ID NO: 7) and 5'-CCG CTC GAG TCA CTG AGT CTT CTG CAG-3' (SEQ. ID NO: 8). SEQ. ID NO: 7 contains a BamHI site at the 5' end and SEQ. ID NO: 8 contains a XhoI site at its 5' end. The amplified DNA was digested with BamHI and XhoI and cloned into pGEX-4T-1 to give pGEX-CD. This DNA construct was used to transform *E. coli* and the fusion protein glutathione-S-transferase-cytidine deaminase was induced with isopropyl-β-D-thiogalatoside and purified on a glutathione affinity chromatographic column. Glutathione-S-transferase was removed from the fusion protein by cleavage with thrombin to give the purified cytidine deaminase (Laliberté et al., 1994, Cancer Res. 54: 5401–5407).

Cell Culture Techniques

Cells were grown in DMEM medium supplemented with 10% heat-inactivated fetal calf serum and 5 µg/ml Gentamycin (DM-10S medium) and incubated at 37° C. and 5% $CO_2$. NIH 3T3 cells, a murine fibroblast cell line which is used frequently in retroviral transduction experiments (In Current Protocols in Molecular Biology, 1989). GP+E86, murine ecotropic packaging cells were described previously (Markowitz et al., 1988, J. Virol. 62: 1120–1124). GP+86E cells were derived from NIH-3T3 cells and contain a stably integrated incompetent retroviral genome; it functions as a retroviral packaging cell line when transfected with plasmids containing a sequence encoding a retroviral mRNA with an intact packaging signal. Plasmid pMFG-CD contains retroviral LTR and an intact packaging signal. GP+E86 cells were transfected with the purified plasmid DNAs pMFG-CD and pSV-neo using the standard calcium phosphate precipitation method (In Current Protocols in Molecular Biology, 1989). 72 hours post-transfection, G418 at 400 µg/ml was added to the medium and the cells were selected in this medium for 14 days. Clones of cells resistant to G418 were isolated by ring cloning or by dilution (Cepko, 1989). Thereafter the cells were maintained in D-10S medium only.

For viral transduction the supernatant from clones of GP+E86 cells was added to the 3T3 cells (Cepko, 1989). 72 hours post-transduction, cytosine arabinoside (ARA-C) at 5 µM was added to the medium and the cells selected in this medium for 14–21 days. Clones resistant to ARA-C were isolated as described above.

Clonogenic assays were performed as follows. The cells were diluted to 100 cells/ml and 1 ml placed in wells of 12-well Costar™ dish. 18–20 hours later, ARA-C was added at the concentrations described in the examples and tables below, and the incubation continued for an additional 15 days. The wells were then stained with 0.5% methylene blue in 50% methanol, and colonies of greater than $10^3$ cells were counted. DNA synthesis assays were performed as follows. Cells were diluted to $10^4$ cells/ml and 1 ml placed in a 12-well Costar dish. After incubation for 4 days, ARA-C was added at the concentrations indicated in the examples and tables below. After an incubation for an additional 16 hours, 0.5 µCi of $^3$H-thymidine (20 Ci/mmol) was added and incubated for a further 4 hours. The amount of radioactivity incorporated into DNA was determined by known methods.

Enzyme Assay

In vitro assay for cytosine deaminase was performed using a modification of a previously described method (Laliberté et al., 1994, Cancer Res. 54: 5401–5407). Briefly, $5 \times 10^7$ monolayer cells were trypsinized, centrifuged and washed once in phosphate buffered saline (PBS), recentrifuged and suspended in 100 µl of 20 mM TrisCl pH 8.0 and 5 mM dithiothreitol. The cell suspension was then subjected to 3 cycles of rapid freezing and thawing. The mixture was centrifuged at maximum speed in a tabletop microfuge at 5° C. for 5 min. The supernatant was used in an assay to measure the conversion of $^3$H-cytidine to $^3$H-uridine.

The present invention will be more readily understood by referring to the following examples which are given to illustrate the invention rather than to limit its scope.

EXAMPLE 1

Cloning of Human Cytidine Deaminase cDNA

FIG. 1 summarizes the cloning process. Cloning of the human cytosine deaminase gene into the eukaryotic expression vector pMFG was performed in the following way. The plasmid pDR-2 containing the cDNA for CD was used as the template for the polymerase chain reaction (PCR). Using a sense primer containing NcoI linker and an antisense primer containing BamHI linker the 438 bp coding region of CD was amplified. The amplified DNA was digested with NcoI and BamHI, purified and cloned into pMFG. The resulting construct was named pMFG-CD. Sequencing of the 5' region of the cytidine deaminase cDNA confirmed the presence of the desired sequence and the start site in pMFG-CD. The sequence of pMFG-CD in the 5'-region of CD is shown. FIG. 1 summarizes the important features from pMFG-CD and contains among other eukaryotic expression elements, the LTR promoter promoting the cytidine deaminase cDNA, and a packaging sequence (necessary for encapsidation of the viral RNA into the virus particle).

EXAMPLE 2

Transfection of Mammalian Cells With pMFG-CD Results in Expression of the Cytidine Deaminase cDNA GP+E86 cells were transfected with pMFG-CD and pSV-neo and 72 hours later placed in medium containing G418 0.5 mg/ml. The cells were incubated in G418 for 14–21 days and then maintained in regular medium. Resistance to the neomycin analog G418 allowed for the enrichment of the population of cells that had taken up the plasmid sequences. These cells were then exposed to ARA-C 5 µM for 14 days and the surviving cells that showed resistance to this cytosine nucleoside analog were cloned to give lines GP+86E-CD3 and GP+86E-CD4.

Figure 2:
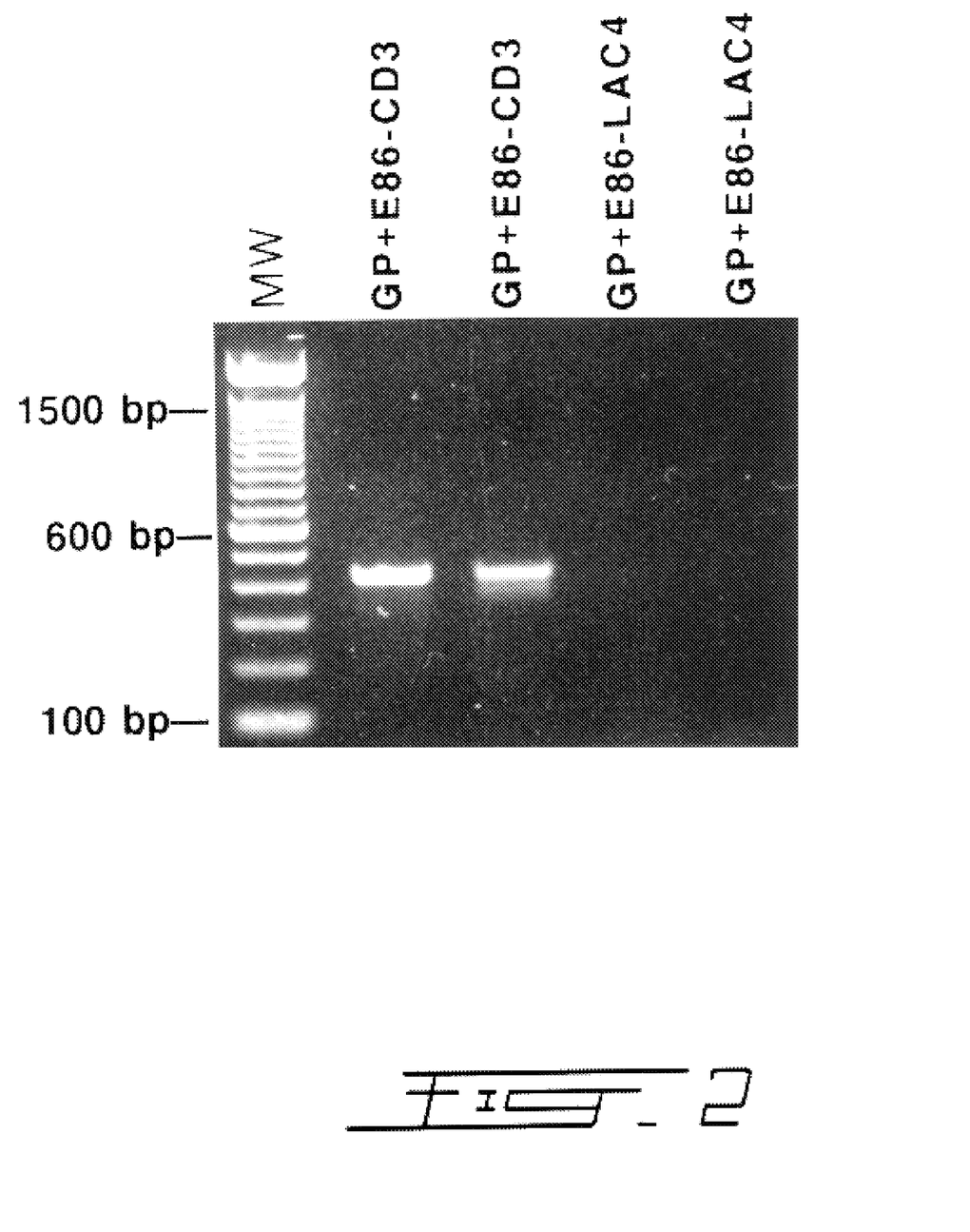
FIG. 2 shows the polymerase chain reaction detecting the presence of the cytidine deaminase cDNA in genomic DNA of GP+E86 cells transfected with pMFG-CD.

Incorporation of the cytidine deaminase cDNA into the genome was demonstrated by genetic analysis of the DNA and the expression of the enzyme. PCR reactions employing primers corresponding to the gag region of pMFG and the coding region of CD were used to amplify the specific DNA of 421 bp as predicted by DNA sequence analysis. FIG. 2 shows the PCR product produced using cellular DNA as template for MFG-CD DNA synthesis. Briefly, genomic DNA (~1 ng) underwent PCR using a sense primer from the 5'-LTR region of MFG and an antisense primer from the coding region of CD. As predicted by the sequence analysis, the amplified DNA had a size of 421 bp. Genomic DNA from non-transfected cells failed to show bands of amplified DNA with the same primers.

These cell populations were also assayed for the expression of cytidine deaminase cDNA. An in vitro assay measured the conversion of radiolabelled cytosine to uridine in lysates of cells. GP+86E-CD3 and GP+86E-CD4 cells showed high levels of cytidine deaminase activity while the non-transfected control cell lines did not (Table 1).

TABLE 1

Conversion of cytidine to uridine in vitro by lysates of cell lines containing the cytidine deaminase gene Cytidine deaminase activity (units/mg)[1]

| Cell line | Exp. 1 | Exp. 2 |
|---|---|---|
| GP + E-86 | 1.0 | |
| GP + E-86-lac 4 | 0.7 | |
| GP + E-86-CD3 | 182.8 | |
| GP + E-86-CD4 | 100.7 | |

[1]Units of activity is defined as nmoles deaminated per min.

EXAMPLE 3

Cell Lines Expressing the Cytidine Deaminase CDNA are Resistant to ARA-C Inhibitory Effects and Toxicity Clonogenic assays were performed to assess the sensitivity of cells to ARA-C. 100 cells were inoculated into tissue culture dish wells and after a 12 day exposure to different concentrations of ARA-C, the number of colonies were counted. Drug resistant cells that can survive and proliferate under these conditions can give rise to individual colonies. The inoculum was dilute enough to allow easy identification and enumeration of individual colonies.

Table 2 demonstrates that cells expressing the cytidine deaminase cDNA can give rise to colonies in the presence of toxic concentrations of ARA-C, due to the inactivation of this cytosine nucleoside analog by deamination. In contradistinction thereto however, cells which do not express the cytidine deaminase cDNA do not form colonies in the presence of toxic concentrations of ARA-C. Indeed, at concentrations of ARA-C of $10^{-6}$ M and higher, cell lines GP+E86-CD3, GP+E86-CD4 and 3T3-CD3-V5 were able to form a significant number of colonies indicating drug resistance to ARA-C, while under these same conditions, the control cell lines GP+E86 and 3T3 did not form any colonies.

TABLE 2

Inhibition of colony formation by different conc. of ARA-C
Average colony count[1]

| Cell line | Exp. No. | Conc. of ARA-C (µM) | | | |
|---|---|---|---|---|---|
| | | 0 | 0.1 | 1.0 | 10.0 |
| GP + 86 | #1 | 28 | 33 | 0 | 0 |
| | #2 | 33 | 29 | 0 | 0 |
| GP + 86-CD3 | #1 | 18 | 25 | 19 | 19 |
| | #2 | | | | |
| GP + 86-CD4 | #1 | 25 | 23 | 24 | 3 |
| | #2 | | | | |
| 3T3 | #1 | 27 | 0 | 0 | 0 |
| | #2 | 31 | 27 | 0 | 0 |
| 3T3-CD3-V5 | #1 | 31 | 34 | 28 | 7 |
| | #2 | | | | |

[1]Cells were exposed to the indicated concentrations of ARA-C for 13 days

Since ARA-C is a potent inhibitor of DNA synthesis, it was important to assess the inhibitory activity of this analog on DNA synthesis in cells expressing CD versus cells not expressing it.

DNA synthesis was measured by the incorporation of radiolabelled thymidine into cellular DNA. As shown in Table 3, ARA-C does not have a very effective inhibitory activity on DNA synthesis in cells expressing the cytidine deaminase cDNA. In cells not expressing the cytidine deaminase cDNA, however, a significant inhibition of DNA synthesis is observed in the presence of ARA-C. Indeed, Table 3 shows that ARA-C at concentration of $10^{-6}$ M and greater, only produced a very weak inhibition of DNA synthesis on cell lines GP+E86-CD3, GP+E86-CD4 and 3T3-CD3-V5. In contrast, in the control cell lines GP+E86 and 3T3, ARA-C produced a potent inhibition of DNA synthesis.

TABLE 3

Inhibition 3H-thymidine incorporation by ARA-C in cell lines expressing cytidine deaminase gene

| Cell line | Additive | cpm ± sem[1] | Inhibition (%) |
|---|---|---|---|
| GP + 86 | none | 1,930 | — |
| | ARA-C 0.5 µm | 2,089 | <1 |

TABLE 3-continued

Inhibition 3H-thymidine incorporation by ARA-C in cell lines expressing cytidine deaminase gene

| Cell line | Additive | cpm ± sem[1] | Inhibition (%) |
|---|---|---|---|
| | ARA-C 1.0 µm | 1,141 | 40.9 |
| | ARA-C 5.0 µm | 551 | 71.5 |
| | ARA-C 10 µm | 316 | 83.6 |
| GP + 86-CD3 | none | 6,374 | — |
| | ARA-C 0.5 µm | 5,831 | 8.5 |
| | ARA-C 1.0 µm | 6,030 | 5.4 |
| | ARA-C 5.0 µm | 5,348 | 16.1 |
| | ARA-C 10 µm | 5,149 | 19.2 |
| GP + 86-CD4 | none | 2,620 | — |
| | ARA-C 1.0 µm | 2,911 | <1 |
| | ARA-C 10 µm | 3,321 | <1 |

[1]cells were incubated with ARA-C for 16 hr followed by addition of $^3$H-thymidine for an additional 5 hr. The numbers indicated have been averaged.

EXAMPLE 4

Retroviral Mediated Gene Transfer Results in Successful Expression of the Cytidine Deaminase cDNA 3T3 cells were transduced by exposure to retroviral particles present in the supernatant from GP+E86-CD3 packaging cells and selected in medium containing ARA-C 5 µM as described in material and methods. The resulting cell line was designated 3T3-CD3-V5. As seen in Table 1, lysates from 3T3-CD3-V5 contained very high levels of cytidine deaminase activity as compared to the control 3T3 cells. The 3T3-CD3-V5 cells were also resistant to ARA-C in clonogenic assays (Table 2), and in DNA synthesis assays (Table 3).

EXAMPLE 5

Expression of Cytidine Deaminase in Prokaryotes

Figure 3:
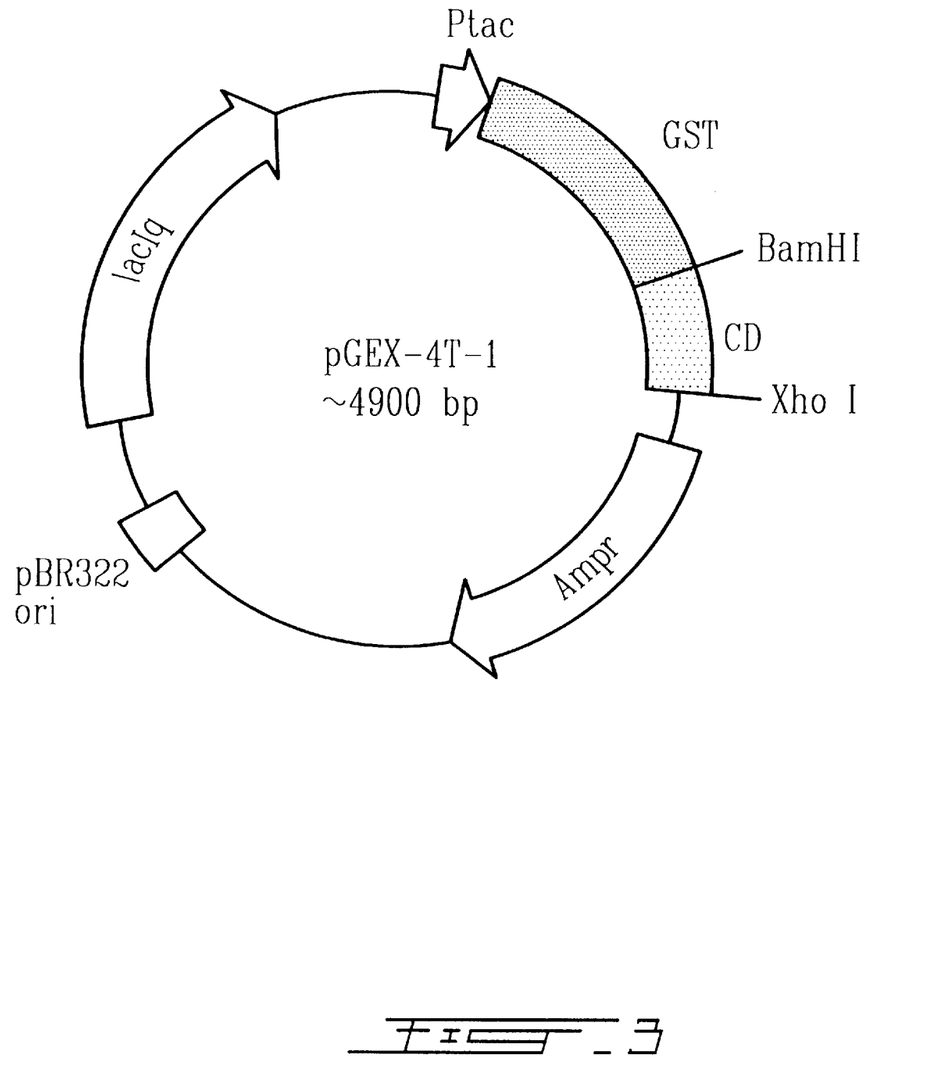
FIG. 3 shows the plasmid DNA construct pGEX-CD containing the human cytidine deaminase gene.
Figure 4:
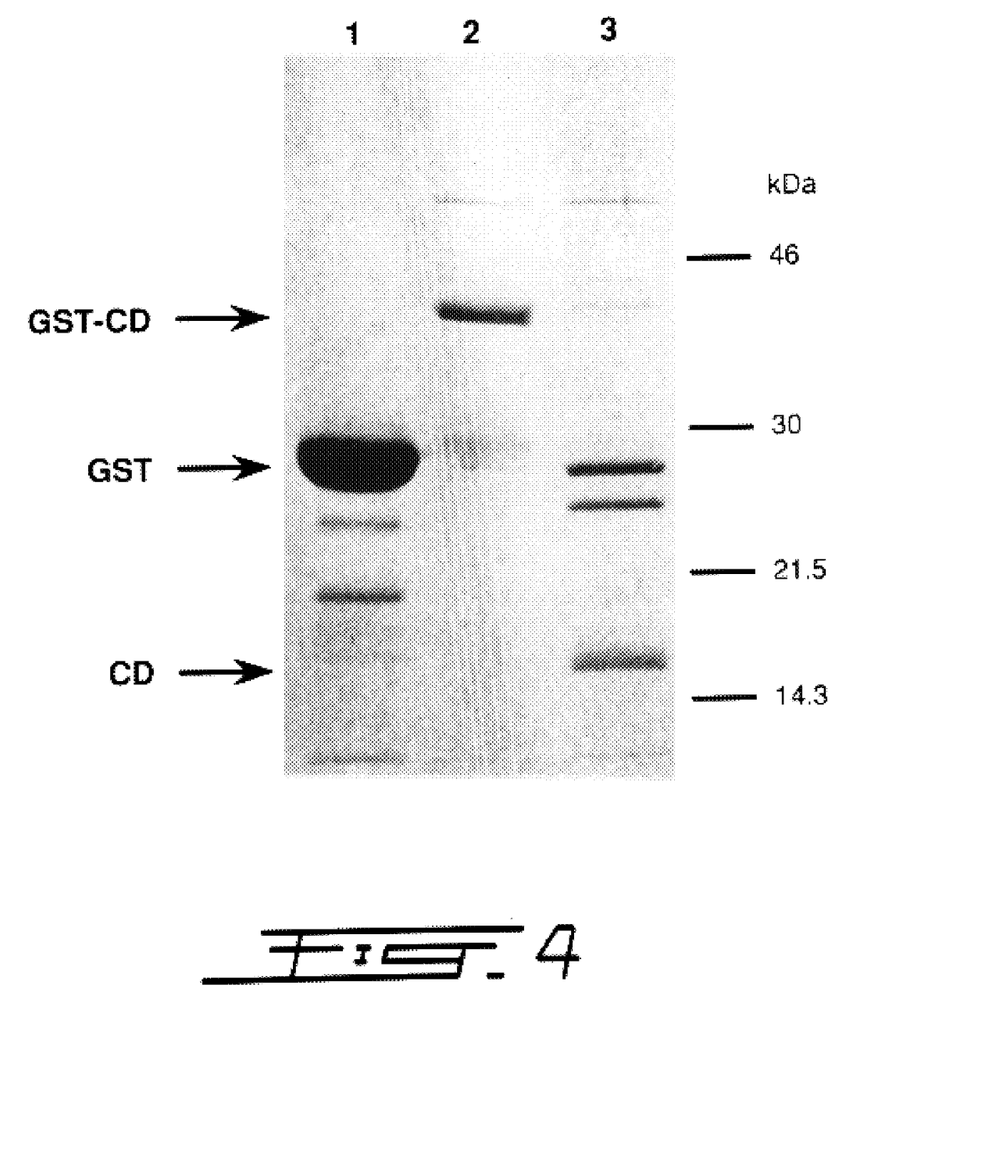
FIG. 4 shows the expression of the CD protein using the expression vector of FIG. 2.

FIG. 3 shows the plasmid pGEX-CD bacterial expression vector. E. coli was transformed with pGEX-CD, the fusion protein glutathione-S-transferase-cytidine deaminase was induced with isopropyl-β-D-thiogalatoside (IPTG) and purified on a glutathione affinity chromatographic column. FIG. 4 shows a sodium dodecyl sulfate-polyacrylamide gel electrophoresis profile of the expression of CD in E. coli. Lane 1 shows the induction of glutathione-S-transferase (GST) (27.5 kDa) induced with IPTG in E. coli transformed with pGEX-4T, a vector which does not contain CD. Lane 2 shows the induction by IPTG of the fusion protein glutathione-S-transferase-cytidine deaminase (GST-CD) (42.4 kDa) from E. coli transformed with pGEX-CD. Lane 3 shows the purified cytidine deaminase (CD) (16.3 kDa) after cleavage of the fusion protein shown in lane 2 with thrombin.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. A eukaryotic expression vector comprising the human cytidine deaminase nucleic acid sequence set forth in SEQ ID NO: 1, wherein said human cytidine deaminase nucleic acid sequence is operably linked to transcription regulatory sequences to confer expression of said human cytidine deaminase by a eukaryotic host cell upon transfection with said eukaryotic expression vector.

2. The eukaryotic expression vector of claim 1, wherein the eukaryotic host cell is a mammalian cell which is resistant to cytosine arabinoside or related cytosine analogs upon expression of said human cytidine deaminase.

3. The eukaryotic expression vector of claim 2, comprising in addition to cytidine deaminase at least one additional nucleic acid sequence expressible in said mammalian cell.

4. The eukaryotic expression vector of claim 3, wherein the additional nucleic acid sequence encodes a dominant selectable marker selected from the group consisting of a dehydrofolate reductase gene, a multidrug resistance gene, a gpt gene and a neomycin gene.

5. The eukaiyotic expression vector of claim 1, which is retroviral expression vector pMFG-CD.

6. The eukaryotic expression vector of claim 1, comprising in addition to cytidine deaminase, at least one additional nucleic acid sequence expressible in said host cell.

7. The eukaryotic expression vector of claim 6, which is retroviral expression vector pMFG-CD.

8. The eukaryotic expression vector of claim 3, which is retroviral expression vector pMFG-CD.

9. An in vitro method of conferring resistance on a mammalian cell to cytosine arabinoside or related cytosine analogs comprising the steps of:

a) transfecting into a producer cell the expression vector of claim 2, thereby producing retroviral particles;

b) transducing a population of mammalian cells with the retroviral vector particles produced by step (a); and c) selecting cytidine deaminase-expressing cells from said transduced cells of step (b) thereby obtaining mammalian cells which express human cytidine deaminase and are resistant to cytosine arabinoside or related cytosine analogs.

10. A eukaryotic cell which comprises the eukaryotic expression vector of claim 1.

11. The eukaryotic cell of claim 10, which is a mammalian cell.

12. An isolated nucleic acid molecule comprising the nucleic acid sequence set forth in SEQ ID NO: 1.

* * * * *

UNITED STATES PATENT AND TRADEMARK OFFICE
CERTIFICATE OF CORRECTION

PATENT NO : 6,083,719
DATED : July 4, 2000
INVENTOR(S) : Richard L. Momparler It is certified that error appears in the above-identified patent and that said Letters Patent are hereby corrected as shown below:

Item [73] Assignee
McGill University is missing as an Assignee.

Signed and Sealed this

First Day of May, 2001

Attest:

NICHOLAS P. GODICI

Attesting Officer     Acting Director of the United States Patent and Trademark Office